(12) United States Patent
Bräunlich et al.

(10) Patent No.: US 6,169,092 B1
(45) Date of Patent: *Jan. 2, 2001

(54) 3-UREIDO-PYRIDOFURANS AND -PYRIDOTHIOPHENES FOR THE TREATMENT OF INFLAMMATORY PROCESSES

(75) Inventors: Gabriele Bräunlich; Mazen Es-Sayed, both of Wuppertal; Rüdiger Fischer, Köln; Rolf Henning, Wuppertal; Burkhard Fugmann, Ratingen; Stephan Schneider; Michael Sperzel, both of Wuppertal, all of (DE); Graham Sturton, Maidenhead (GB); Mary Fitzgerald, Yarnton (GB); Barbara Briggs, Kingston (GB); Arnel Concepcion, Nara (JP)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/214,370

(22) PCT Filed: Jul. 1, 1997

(86) PCT No.: PCT/EP97/03432

§ 371 Date: Jan. 5, 1999

§ 102(e) Date: Jan. 5, 1999

(87) PCT Pub. No.: WO98/02440

PCT Pub. Date: Jan. 22, 1998

(30) Foreign Application Priority Data

Jul. 12, 1996 (GB) .................................................. 9614718

(51) Int. Cl.[7] .................. A61K 31/495; A61K 31/44; C07D 408/02; C07D 491/00; C07D 515/02
(52) U.S. Cl. .................. 514/258; 514/302; 514/291; 514/301; 546/116; 546/89; 546/114; 544/253
(58) Field of Search ............................ 544/253; 514/258, 514/302, 291, 301; 546/116, 89, 114

(56) References Cited

U.S. PATENT DOCUMENTS

| 4,455,427 | 6/1984 | Johnson . |
|---|---|---|
| 4,663,347 | 5/1987 | Atkinson et al. . |
| 5,377,477 | 1/1995 | Haberstroh et al. . |
| 5,504,213 | 4/1996 | Fischer et al. . |
| 5,565,488 | 10/1996 | Braunlich et al. . |
| 5,622,989 | 4/1997 | Braunlich et al. . |
| 5,922,740 | 7/1999 | Braunlich et al. . |

FOREIGN PATENT DOCUMENTS

| 0 069 521 | 1/1983 | (EP) . |
|---|---|---|
| 0 146 243 | 6/1985 | (EP) . |
| 0 551 662 | 7/1993 | (EP) . |
| 0 623 607 | 11/1994 | (EP) . |
| 0 685 474 | 12/1995 | (EP) . |
| 0 685 475 | 12/1995 | (EP) . |
| 0 685 479 | 12/1995 | (EP) . |
| 0 731 099 | 9/1996 | (EP) . |
| 0 779 291 | 6/1997 | (EP) . |

OTHER PUBLICATIONS

Ried, Walter et. al., Reaction of 2–benzoyl–3–chloro–1–benzothiophene–1,1–dioxide with sulfur compounds, Chem. Ber., vol. 110 (4), pp. 1356–1363, 1977.*
Biochen J. 291, 389–395, 1993.
Biochen, Pharmacol. 42, 153–162, 1991.
Eur. J. Pharmacol. 127, 105–115, 1986.

* cited by examiner

*Primary Examiner*—John Kight
*Assistant Examiner*—Binta Robinson
(74) *Attorney, Agent, or Firm*—Norris McLaughlin & Marcus P.A.

(57) ABSTRACT

3-Urea-pyridofurans and -pyridothiophenes are prepared by reacting appropriately substituted 3-amino-pyridofurans or -pyridothiophenes with isocyanates or isothiocyanates. The 3-urea-pyridofurans and -pyridothiophenes can be used as active ingredients in medicaments, particularly in medicaments for the treatment of acute and chronic inflammatory processes.

7 Claims, No Drawings

3-UREIDO-PYRIDOFURANS AND -PYRIDOTHIOPHENES FOR THE TREATMENT OF INFLAMMATORY PROCESSES

This application is a 371 of PCT/EP97/03432. Filed Jul. 1, 1997.

The invention relates to 3-urea-pyridofurans and -pyridothiophenes, processes for their preparation and their use in medicaments.

It is known that the NADPH oxidase of phagocytes is the physiological source to the superoxide radical anion and reactive oxygen species derived therefrom which are important in the defence against pathogens. Moreover, both inflammatory (e.g. TNFα, IL-1 or IL-6) and anti-inflammatory cytokines (e.g. L-10) play a pivotal role in host defence mechanisms. Uncontrolled production of inflammatory medicators can lead to acute and chronic inflammation, tissue damage, multi-organ failures and to death. It is additionally known that elevation of phagocyte cyclic AMP leads to inhibition of oxygen radical production and that this cell function is more sensitive than others such as aggregation or enzyme release.

Benzofuran- and benzothiophene derivatives having lipoxygenase-inhibiting action are described in the publication EP 146 243.

The invention relates to 3-urea-pyridofurans and -pyridothiophenes of the general formula (I)

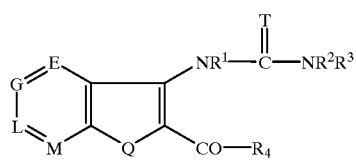

in which

E, G, L and M are identical or different and represent a nitrogen atom or a residue of a formula —C—A, wherein at least one of the substituents E, G, L or M must represent a nitrogen atom and wherein A represents hydrogen, straight-chain or branched acyl or alkoxy-carbonyl each having up to 6 carbon atoms or straight-chain or branched alkyl having up to 6 carbon atoms, which is optionally substituted by carboxyl, halogen, hydroxyl, straight-chain or branched alkoxycarbonyl, or alkoxy each having up to 6 carbon atoms, phenoxy, benzoyl or by a group of a formula —O—CO—CH$_3$, or represents halogen, carboxyl, cyano, nitro, trifluoromethyl, trifluoromethoxy or a group of a formula —OR$^5$, —S(O)$_a$R$^6$, —(O—CH$_2$—CO)$_b$—NR$^7$R$^8$, —CO—NR$^9$R$^{10}$, —SO$_2$—NR$^{11}$R$^{12}$ or —NH—SO$_2$R$^{13}$, in which R$^6$, R$^8$, R$^{10}$ and R$^{12}$ are identical or different and denote hydrogen, cycloalkyl having 3 to 6 carbon atoms, benzyl or a 5 to 7-membered saturated or unsaturated heterocycle having up to 3 heteroatoms from the series comprising N, S and O and to which a phenyl ring can be fused and which is optionally substituted by identical or different substituents from the series comprising halogen, cyano, nitro or by a straight-chain or branched alkyl having up to 6 carbon atoms or denote straight-chain or branched alkenyl or acyl each having up to 8 carbon atoms, or denote phenyl, which is optionally monosubstituted to disubstituted by identical or different substituents from the series comprising nitro, halogen, carboxy or straight-chain or branched alkoxycarbonyl having up to 6 carbon atoms, R$^7$, R$^9$ and R$^{11}$ are identical or different and denote hydrogen or a straight-chain or branched alkyl having up to 4 carbon atoms, or R$^7$ and R$^8$ together with the nitrogen atom form a 5- to 6-membered heterocycle, R$^5$ has the abovementioned meaning of R$^6$, R$^8$, R$^{10}$ or R$^{12}$ and is identical or different from the latter, or R$^5$ denotes a hydroxyl protecting group or straight-chain or branched alkoxycarbonyl having up to 6 carbon atoms, or denotes straight-chain or branched alkyl having up to 8 carbon atoms, which is optionally substituted by carboxyl, hydroxyl, straight-chain or branched acyl, oxyacyl or alkoxy-carbonyl each having up to 6 carbon atoms, phenoxy, benzoyl or by a 5- to 7-membered unsaturated heterocycle having up to 3 heteroatoms from the series comprising N, S and/or O, which is optionally substituted by halogen, cyano, nitro, or by straight-chain or branched alkyl having up to 6 carbon atoms, and/or alkyl is substituted by a (group of a formula —(CO)$_c$—NR$^{14}$R$^{15}$ in which R$^{14}$ and R$^{15}$ are identical or different and have the above-mentioned meaning of R$^7$ and R$^8$ and c denotes a number 0 or 1, or R$^5$ denotes a group of the formula —SO$_2$—R$^{16}$ R$^{16}$ denotes phenyl, trifluoromethyl or straight-chain or branched alkyl having up to 4 carbon atoms, a denotes a number 0, 1 or 2, b denotes a number 0 or 1, R$^{13}$ has the abovementioned meaning of R$^{16}$ and is identical or different from the latter.

or

E and G represent the CH-group and

L and M represent a residue of a formula —CD and —CD' in which

D and D' together form a pyridine ring,

R$^1$ represents hydrogen, straight-chain or branched alkyl having up to 6 carbon atoms, an aminoprotecting group or a group of the formula —CO—R$^{17}$ in which R$^{17}$ denotes hydroxyl, straight chain or branched alkoxycarbonyl having up to 6 carbon atoms, cycloalkyl having 3 to 6 carbon atoms, pyridyl, pyrrolidinyl or straight chain or branched alkyl having up to 8 carbon atoms, which is optionally substituted by halogen, carboxyl or straight chain or branched alkoxycarbonyl having up to 6 carbon atoms, or denotes phenyl, which is optionally substituted by hydroxyl, carboxyl or straight chain or branched alkoxy or alkoxycarbonyl each having up to 6 carbon atoms, T represents an oxygen or sulfur atom, R$^2$ and R$^3$ are identical or different and represent hydrogen, cycloalkyl having up to 6 carbon atoms, straight chain or branched alkyl, alkoxycarbonyl or alkenyl each having up to 8 carbon atoms, or represent benzoyl or aryl having 6 to 10 carbon atoms, which are optionally monosubstituted to trisubstituted by identical or different subsubstituents from the series comprising halogen, cyano, nitro, carboxyl, straight-chain or branched alkyl, alkoxy, alkoxycarbonyl or acyl each having up to 6 carbon atoms, or represent a group of a formula —P(O)(OR$^{18}$(OR$^{19}$),
in which $R^{18}$ and $R^{19}$ are identical or different and denote hydrogen or straight chain or branched alkyl having up to 6 carbon atoms, or $R^2$ and $R^3$ together with the nitrogen atom form a 5- to 7-membered saturated heterocycle optionally having a further O atom, and $R^4$ represents aryl having 6 to 10 carbon atoms or represents a 5 to 7 membered, saturated or unsaturated heterocycle, which can contain up to 4 oxygen, sulphur and/or nitrogen atoms as heteroatoms and to which further a benzene ring can be fused and wherein both rings are optionally monosubstituted to trisubstituted by identical or different substituents from the series comprising hydroxyl, halogen, nitro, 1H-tetrazolyl, pyridyl, trifluoromethyl, trifluoromethoxy, difluoromethyl, difluoromethoxy, cyano, carboxy, straight-chain or branched alkoxy, alkoxycarbonyl or acyl each having up to 8 carbon atoms or by straight-chain or branched alkyl having up to 6 carbon atoms, which is optionally substituted by carboxyl or straight-chain or branched alkoxycarbonyl having up to 5 carbon atoms or by a group of a formula —NR$^{20}$R$^{21}$—, —SR$^{22}$, SO$_2$R$^{23}$ or —O—SO$_2$R$^{24}$,
in which $R^{20}$ and $R^{21}$ have the meaning shown above for $R^7$ and $R^8$, or $R^{20}$ denotes hydrogen, and $R^{21}$ denotes straight-chain or branched acyl having up to 6 carbon atoms, $R^{22}$ denotes straight-chain or branched alkyl having up to 6 carbon atoms, $R^{23}$ and $R^{24}$ are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, Q represents an oxygen or sulfur atom, and salts thereof.

The 3-urea-pyridofurans and -pyridothiophenes according to the invention can also be present in the form of their salts and pyridinium salts. In general, salts with organic or inorganic bases or acids may be mentioned here.

Physiologically acceptable salts are preferred in the context of the present invention. Physiologically acceptable salts of the 3-urea-pyridofurans and -pyridothiophenes can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid. Preferred pyridinium salts are salts in combination with halogen.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Heterocycle in general represents a 5- to 7-membered saturated or unsaturated, preferably 5- to 6- membered, saturated or unsaturated ring which can contain up to 4 oxygen, sulphur and/or nitrogen atoms as heteroatoms and to which further aromatic ring can be fused.

The following are mentioned as preferred: thienyl, furyl, pyrrolyl, pyridyl, pyrimidyl, pyrazinyl, pyridazinyl, quinolyl, isoquinolyl, quinazolyl, quinoxazolyl, cinnolyl, thiazolyl, dihydrothiazolyl, benzothiaazolyl, isothiazolyl, benzisothiazolyl, oxazolyl, benzoxazolyl, isoxazolyl, imidazolyl, benzimidazolyl, indolyl, morpholinyl, pyrrolidinyl, piperidyl, piperazinyl, oxazolyl, oxazolinyl or triazolyl.

Amino protective group in the context of the above mentioned definition in general represents a protective group from the series comprising: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyl oxycarbonyl, 4-nitrobenzyl oxycarbonyl, 2-nitrobenzyl oxycarbonyl, 2-nitro-4,5-dimethoxyb enzyloxycarbonyl, methoxycarbonyl, ethoxycarbonyl, propoxycarbonyl, isopropoxycarbonyl, butoxycarbonyl, isobutoxycarbonyl, tert.butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichlorethoxycarbonyl, 2,2,2-trichlor-tertbutoxycarbonyl, menthyloxycarbonyl, phenoxycarbonyl, 4-nitrophenoxycarbonyl, fluorenyl-9-methoxycarbonyl, formyl, acetyl, propionyl, pivaloyl, 2-chloracetyl, 2-bromacetyl, 2,2,2-trifluoracetyl, 2,2,2-trichloracetyl, benzoyl, 4-chlorbenzoyl, 4-brombenzoyl, 4-nitrobenzoyl, phthalimido, isovaleroyl oder benzyloxymethylen, 4-nitrobenzyl, 2,4-dinitrobenzyl or 4-nitrophenyl.

Preferred compounds of the general formula (I) are those in which

E, G, L and M are identical or different and represent a nitrogen atom or a residue of a formula —C—A, wherein at least one of the substituents E, G, L or M must represent a nitrogen atom and wherein A represents hydrogen, straight-chain or branched acyl or alkoxycarbonyl each having, up to 6 carbon atoms, or straight-chain or branched alkyl having up to 5 carbon atoms, which is optionally substituted by chlorine, bromine, hydroxyl, carboxyl, straight-chain or branched alkoxycarbonyl or alkoxy each having up to 5 carbon atoms, phenoxy, benzoyl, or by a group of a formula —O—CO—CH$_3$, or represents fluorine, chlorine, bromine, nitro, trifluoromethyl or a group of a formula —OR$^5$, —S(O)$_n$R$^6$, (O—CH$_2$—CO)$_n$—

$NR^7R^8$, $-CO-NR^9R^{10}$, $-SO_2-NR^{11}R^{12}$ or $-NH-SO_2R^{13}$, in which $R^6$, $R^8$, $R^{10}$ and $R^{12}$ are identical or different and denote hydrogen, cyclopropyl, cyclopentyl, cyclohexyl, chinolyl, pyridyl, imidazolyl, 1,3-thiazolyl or thienyl, which are optionally substituted by identical or different subltituents from the series comprising fluorine, chlorine, bromine, iodine, cyano, nitro or by a straight-chain or branched alkyl having up to 5 carbon atoms, denote straight-chain or branched alkyl, alkenyl or acyl each having up to 6 carbon atoms, or denote phenyl, which is optionally monosubstituted to disubstituted by identical or different substituents from the series comprising nitro, fluorine, chlorine, bromine, iodine, carboxyl or straight-chain or branched alkoxycarbonyl having, up to 5 carbon atoms, $R^7$, $R^9$ and $R^{11}$ are identical or different and denote hydrogen or a straight-chain or branched alkyl having up to 3 carbon atoms, or $R^7$ and $R^8$ together with the nitrogen atom form a pyrrolidinyl or piperidinyl ring, $R^5$ has the abovementioned meaning of $R^6$, $R^8$, $R^{10}$ or $R^{12}$ and is identical or different from the latter, or $R^5$ denotes benzyl, acetyl or tetrahydropyranyl or straight chain or branched alkoxycarbonyl having up to 4 carbon atoms, denotes straight-chain or branched alkyl having up to 6 carbon atoms, which is optionally substituted by carboxyl, hydroxyl, straight-chain or branched acyl, oxyacyl or alkoxycarbonyl each having up to 4 carbon atoms, phenoxy, benzoyl or by pyridyl, imidazolyl, thenyl or furyl, which are optionally substituted by fluorine, chlorine, bromine, cyano, nitro or by straight-chain or branched alkyl having up to 4 carbon atoms, and/or alkyl is substituted by a group of a formula $-(CO)_c-NR^{14}R^{15}$, in which $R^{14}$ and $R^{15}$ are identical or different and have the above mentioned meaning of $R^7$ and $R^8$, and c denotes a number 0 or 1, or $R^5$ denotes a group of a formula $-SO_2R^{16}$, in which $R^{16}$ denotes phenyl, trifluoromethyl or straight-chain or branched alkyl having up to 3 carbon atoms, a denotes a number 0, 1 or 2, b denotes a number 0 or 1, $R^{13}$ has the abovementioned meaning of $R^{16}$ and is identical or different from the latter, or E and G represent the CH-group, and L and M represent a residue of a formulae —CD and —CD', in which D and D' together form a pyridine ring, $R^1$ represents hydrogen, straight-chain or branched alkyl having up to 4 carbon atoms, tert.butoxycarbonyl or a group of the formula $-CO-R^{17}$ in which $R^{17}$ denotes hydroxyl, straight chain or branched alkoxycarbonyl having up to 4 carbon atoms, cyclopentyl, cyclohexyl, pyridyl, pyrrolidinyl or straight chain or branched alkyl having up to 5 carbon atoms, which is optionally substituted by fluorine, chlorine, bromine, carboxyl or straight chain or branched alkoxycarbonyl having up to 4 carbon atoms, or denotes phenyl, which is optionally substituted by hydroxyl, carboxyl or straight chain or branched alkoxy or alkoxycarbonyl each having up to 4 carbon atoms, T represents an oxygen or sulfur atom, $R^2$ and $R^3$ are identical or different and represent hydrogen, cyclobutyl, cyclopentyl, cyclohexyl or straight-chain or branched alkyl, alkoxycarbonyl or alkenyl each having up to 6 carbon atoms, or represent benzoyl or phenyl, which are optionally monosubstituted to trisubstituted by identical or different substituents from the series comprising fluorine, chlorine, bromine, iodine, carboxyl, cyano, nitro or by a straight-chain or branched alkyl, alkoxy or alkoxycarbonyl each having up to 5 carbon atoms, or represent a group of a formula $-P(O)(OR^{18})(OR^{19})$ in which $R^{18}$ and $R^{19}$ are identical or different and denote straight chain or branched alkyl having up to 4 carbon atoms or $R^2$ and $R^3$ together with the nitrogen atom form a pyrrolidinyl, piperidinyl or morpholinyl ring, and $R^4$ represents phenyl or represents pyridyl, pyrimidyl, pyrryl, imidazolyl, pyrazolyl, thienyl, isothiazolyl, pyrazinyl, thiazolyl or benzo[b]thiophenyl, wherein both rings are optionally monosubstituted to trisubstituted by identical or different substituents from the series comprising hydroxyl, fluorine, chlorine, bromine, nitro, tetrazolyl, pyridyl, trifluoromethyl, trifluoromethoxy, difluoromethyl, difluoromethoxy, cyano, carboxy, straight-chain or branched alkoxy, alkoxycarbonyl or acyl each having, up to 6 carbon atoms, or by straight-chain or branched alkyl having up to 4 carbon atoms, which is optionally substituted by carboxyl or straight-chain or branched alkoxycarbonyl having up to 4 carbon atoms, and Q represents an oxygen or sulfur atom, and salts thereof.

Particularly preferred compounds of the general formula (I) are those, in which

E, G, L and M are identical or different and represent a nitrogen atom or a residue of a formula —C—A, wherein at least one of the substituents is E, G, L or M, must represent a nitrogen atom and wherein A represents hydrogen, acetyl, straight-chain or branched alkoxy, or alkoxycarbonyl having up to 4 carbon atoms, straight-chain or branched alkyl having up to 5 carbon atoms, which is optionally substituted by bromine or by a group of a formula $O-CO-CH_3$, methoxy or hydroxyl or represents fluorine, chlorine, bromine, carboxyl, cyano, hydroxyl, nitro, trifluoromethyl, or a group of the formula $-OSO_2-CH_3$, $-OCH_2-CH=CH_2$, $-O-CH_2-CO$-pyrrolidine, $-O(CH_2)_2$-pyrrolidine, $-O(CH_2)_2$-piperidine, $-O-(CH_2)_4-O-C(O)-CH_3$ or $-O-(CH_2)_2-O-C(O)-CH_3$ or E and G represents the CH-group, and L and M represent a residue of a formulae —CD and —CD' in which
D and D' together form a pyridine ring,
R¹ represents hydrogen or straight-chain or branched alkyl having up to 3 carbon atoms,
T represents an oxygen or sulfur atom,
R² and R³ are identical or different and represent hydrogen, straight-chain or branched alkyl having up to 5 carbon atoms, or represent benzoyl or phenyl, or represent a group of a formula —P(O)(OC₂H₅)₂,
and
R⁴ represents phenyl or represents pyridyl, pyrimidyl, furyl, thienyl, imidazolyl, pyrrolyl, thiazolyl or pyrazinyl which are optionally up to difold substituted by identical or different pyridyl, nitro, fluorine, chlorine, bromine, methoxy, trifluoromethyl, cyano, or by straight-chain or branched alkyl having up to 3 carbon atoms, which is optionally substituted by carboxyl or straight-chain or branched alkoxycarbonyl having up to 3 carbon atoms
and
Q represents an oxygen or sulfur atom,
and salts thereof.

Very particularly preferred are those compounds of the general formula (I),
in which
R¹ and R² represent hydrogen,
R⁴ represents phenyl, pyridyl or thienyl, which are optionally mono- or disubstituted by chlorine, bromine, fluorine, nitro, methoxy or straight-chain or branched alkyl having up to 3 carbon atoms.

A process for the preparation of the compounds of the general formula (I) has additionally been found, characterized in that
compounds of the general formula (II)

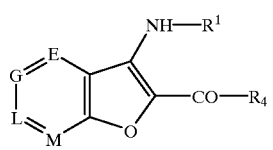

in which
E, G, L, M, R¹ and R⁴ have the abovementioned meaning are reacted with compounds of the general formula (III)

$$R^{25}—N=C=T \qquad (III)$$

in which
T has the abovementioned meaning
and
R²⁵ has the abovementioned meaning of R² and R³
in inert solvents, if appropriate in the presence of a base and/or in the presence of an auxiliary,
and in the case of R²/R³=H and T=O,
compounds of the general formula (II) are reacted with compounds of the general formula (IIIa)

$$V—SO_2—N=C=O \qquad (IIIa)$$

in which
V denotes halogen, preferably chlorine,
and in the case of R²/R³=H and T=S,
compounds of the general formula (II) are reacted with NH₄SCN,
and in case of R¹, R² and/or R³≠H the amino groups are derivatized optionally by customary methods.

and in the case of A=O—SO₂R¹⁶ the corresponding hydroxyl compounds are reacted with sulfonyl chloride derivatives in presence of K₂CO₃.

The process according to the invention can be illustrated by way of example by the following equations:

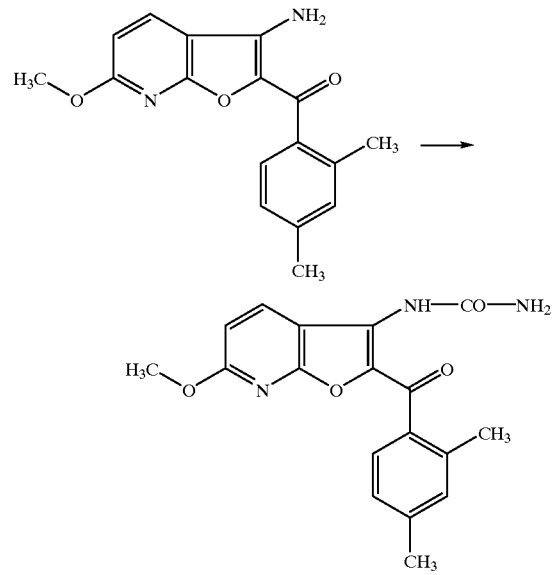

Suitable solvents are generally customary organic solvents which do not change under the reaction conditions. These include ethers such as diethyl ether, dioxane or tetrahydrofurane, ethylacetate, acetone, dimethylsulfoxide, dimethylformamide or alcohols such as methanol, ethanol, propanol or halogenohydrocarbons such as dichloromethane, dichloroethane, trichloromethane or tetrachloromethane. Dichloromethane is preferred.

Suitable bases are generally inorganic or organic bases. These preferably include alkali metal hydroxides such as, for example, sodium hydroxide, sodium hydrogen-carbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal or organic amines (trialkyl(C₁–C₆)amines) such as triethylamine, or heterocycles such as 1,4-diazabicyclo[2.2.2]octane (DABCO), 1,8-diazabicyclo[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodium-hydroxide are preferred.

The process is in general carried out in a temperature range from −30° C. to +100° C., preferably from −10° C. to +50° C.

The process is generally carried out at normal pressure. However, it is also possible to carry out it at elevated pressure or at reduced pressure (for example in a range from 0.5 to 5 bar).

The base is employed in an amount from 1 mol to 10 mol, preferably from 1.0 mol to 4 mol, relative to 1 mol of the compounds of the general formulae (III) or (IIIa).

The compounds of the general formula (II) are in the case of E=N new or are prepared by at first reacting compounds of the general formula (IV)

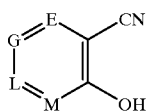

(IV)

in which
E, G, L and M have the above mentioned meaning
with compounds of the general formula (V)

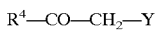

R$^4$—CO—CH$_2$—Y  (V)

in which
R$^4$ has the abovementioned meaning
and
Y represents a typical leaving group such as, for example, chlorine, bromine, iodine, tosylate or mesylate, preferably bromine,
to form compounds of the general formula (VI)

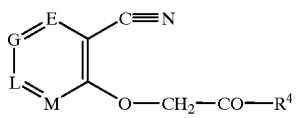

(VI)

in which
E, G, L, M and R$^4$ have the abovementioned meaning, and followed by cyclisation,
in one of the abovementioned solvents and bases, preferably potassium carbonate and dimethylformamide or acetone, and in the case of R$^1$≠H the abovementioned substitutents are introduced by customary methods.

The process is in general carried out in a temperature range from +10° C. to +150° C., preferably from +50° C. to +100° C.

The process is generally carried out at normal pressure. However, it is also possible to carry out it at elevated pressure or at reduced pressure (for example in a range from 0.5 to 5 bar).

Suitable bases are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert.butoxide. Sodium hydroxide or potassium hydroxide are particularly preferably employed.

Suitable solvents are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Alcohols such as methanol, ethanol, propanol or isopropanol are particularly preferably used. It is also possible to employ mixtures of the solvents mentioned.

The reaction can also be carried out with acids such as, for example, trifluoroacetic acid, acetic acid, hydrochloric acid, hydrobromic acid, methanesulphonic acid, sulphuric acid or perchloric acid, preferably with trifluoroacetic acid.

The reaction is in general carried out in a temperature range from 0° C. to +180° C., preferably from +20° C. to +160° C.

In general, the reaction is carried out at normal pressure. However, it is also possible to work at reduced pressure or at elevated pressure (for example from 0.5 to 5 bar).

When carrying out the reaction, the base is in general employed in an amount from 1 to 3 mot, preferably from 1 to 1.5 mol, relative to 1 mol of the ester. Molar amounts of the reactants are particularly preferably used.

Compounds of the general formula (II) in which M denotes a nitrogen atom are prepared by reacting compounds of the general formula (IVa)

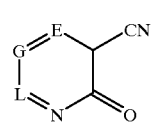

(IVa)

in which
E, G and L have the abovementioned meaning,
in analogy to the abovementioned process.

The compounds of the general formula (IV) are new or can prepared by at first reacting compounds of the general formula (VII)

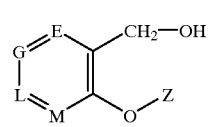

(VII)

in which
E, G, L and M have the abovementioned meaning
and
Z represents C$_1$–C$_4$-alkyl
with MnO$_2$ and followed by BCl$_3$/dimethylaminopyridine,
to form compounds of the general formula (VIII)

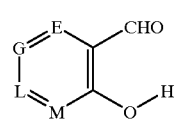

(VIII)

in which
E, G, L and M have the abovementioned meaning
and in a last step are reacting with NH$_2$OH/HCl/HCOOH.

The reaction is in general carried out in a temperature range from 0° C. to +180° C., preferably from +20° C. to +160° C.

In general, the reaction is carried out at normal pressure. However, it is also possible to work at reduced pressure or at elevated pressure (for example from 0.5 to 5 bar).

The compounds of the general formula (VII) are new or are prepared by customary methods for example by reducting of the corresponding carboxyl group by LiAlH$_4$ in one of the abovementioned ethers.

The compounds of the general formulae (III), (IIa), (IV), (IVa) and (V) are known or can be prepared by customary methods.

The compounds of the general formulae (VI) and (VIII) are new or can be prepared like described above.

Surprisingly it was found that compounds given by the general formula (I) inhibited oxygen radical formation as well as TNFα (tumor necrosis factor) production. These compounds elevated cellular cyclic AMP probably by inhibition of phagocyte phosphodiesterase activity.

The compounds according to the invention specifically inhibit the production of superoxide by polymorphonuclear leukocytes (PMN). Furthermore, these compounds inhibit TNFα release in human monocytes in response to a variety of stimuli including bacterial lipopolysaccharide (LPS), complement-opsonized zymosan (ZymC3b) and IL-Iβ. The described effects are probably mediated by the elevation of cellular cAMP probably due to inhibition of the type IV phosphodiesterase responsible for its degradation.

They can therefore be employed in medicaments for the treatment of acute and chronic inflammatory processes.

The compounds according to the invention are preferably suitable for the treatment and prevention of acute and chronic inflammation and auto immune diseases, such as emphysema, alveolitis, shock lung, all kind of COPD, ARDS, asthma and bronchitis, cystic fibrosis, eosinophilic granuloma, arteriosclerosis, arthrosis, inflammation of the gastro-intestinal tract, myocarditis, bone resorption diseases, reperfusion injury, Crohn's disease, ulcerative colitis, system lupus erythematosus, type I diabetes mellitus, psoriasis, anaphylactoid purpura nephritis, chronic glomerulonephtritis, inflammatory bowel disease, other benign and malignant proliferative skin diseases, atopic dermatitis, allergic rhinitis, allergic conjunctivitis, vernal conjunctivitis, arterial restenosis, sepsis and septic shock, toxic shock syndrome, grafts vs host reaction, allograft rejection, treatment of cytokine mediated chronic tissue degeneration, rheumatoid arthritis, arthritis, rheumatoid spondylitis and osteoarthritis and coronary insufficiency, myalgias, multiple sclerosis, malaria, AIDS, cachexia, prevention of tumor growth and invasion of tissue, leukemia, depression, memory impairment and acute stroke. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test description

1. Preparation of human PMN

Blood was taken from healthy subjects by venous puncture and neutrophils were purified by dextran sedimentation and resuspended in the buffered medium.

2. Inhibition of FMLP-stimulated production of superoxide racidal anions.

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 μM, the DMSO concentration was 0.1% v/v in all wells. After addition of cytochalasin b (5 μg×ml$^{-1}$) the plate was incubated for 5 min at 37° C. Neutrophils were then stimulated by addition of $4 \times 10^{-8}$ M FMLP and superoxide generation measured as superoxide dismutase inhibitable reduction of cytochrome C by monitoring the OD$_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1 - ((Rx - Rb))]}{((Ro - Rb))} \times 100$$

Rx=Rate of the well containing the compound according to the invention.
Ro=Rate in the control well.
Rb=Rate in the superoxide dismutase containing blank well.

Compounds according to the invention have IC$_{50}$ values in the range 0,07 μM–10 μM.

3. Measurement of PMN cyclic AMP concentration

The compounds according to the invention were incubated with $3.7 \times 10^6$ PMN for 5 min at 37° C. before addition of $4 \times 10^{-8}$ M FMLP. After 6 min protein was precipitated by the addition of 1% v/v conc. HCl in 96% v/v ethanol containing 0.1 mM EDTA. After centrifugation the ethanolic extracts were evaporated to dryness under N$_2$ and resuspended in 50 mM Tris/HCl pH 7.4 containing 4 mM EDTA. The cyclic AMP concentration in the extracts was determined using a cyclic AMP binding protein assay supplied by Amersham International plc. Cyclic AMP concentrations were expressed as percentage of vehicle containing control incubations.

Compounds elavate the cAMP-level at 1 μM compound 0–400% of control values.

4. Assay of PMN phosphodiesterase

This was performed as a particulate fraction from human PMN essentially as described by Souness and Scott (Biochem. J. 291, 389–395, 1993). Particulate fractions were treated with sodium vanadate/glutathione as described by the authors to express the descrete stereospecific site on the phosphodiesterase enzyme. Compounds according to the invention had lC$_{50}$ values ranging from 0,001 μM to 10 μM.

5. Assay of human platelet phosphodiesterase

This was performed essentially as described by Schmidt et at (Biochem. Pharmacol. 42, 153–162, 1991) except that the homogenate was treated with vanadate glutathione as above. Compounds according to the invention had IC$_{50}$ values greater than 100 μM.

6. Assay of binding to the rolipram binding site in rat brain membranes

This was performed essentially as described by Schneider et al. (Eur. J. Pharmacol. 127, 105–115, 1986). Compounds according to the invention had IC$_{50}$ values in the range 0,01 to 10 μM.

7. Preparation of human monocytes

Blood was taken from normal donors. Monocytes were isolated from peripheral blood by density centrifugation, followed by centrifugal elutriation.

8. Endotoxin induced TNF release

Monocytes ($1 \times 10^6$ ml$^{-1}$) were stimulated with LPS (2 μg ml$^{-1}$) and coincubated with the compounds at different concentrations ($10^{-4}$ to 10 μg ml$^{-1}$). Compounds were dissolved in DMSO/medium (2% v/v). The cells were incubated in RPMI-1640 medium glutamine/FCS supplemented and at 37° C. in a humidified atmosphere with 5% CO$_2$. After 18 to 24 hours TNF was determined in the supernatants by an human TNF specific ELISA (medgenix). Controls were nonstimulated and LPS stimulated monocytes without compounds. Example 2, 13 and 16 induce inhibition of LPS driven TNF activity in human monocytes (IC$_{50}$: $10^{-3}$ to 1 μg ml$^{-1}$).

9. Endotoxin induced shock lethality in mice

B6D2F1 mice (n=10) were sensitized with galactosamine (600 mg/kg), and shock and lethality were triggered by LPS (0.01 μg/mouse). The compounds were administered intravenously 1 hour prior LPS. Controls were LPS challenged mice without compound. Mice were dying 8 to 24 hours post LPS challenge. Example 1 and 9 reduced the endotoxin medicated mortality about 70% to 100% at doses of 3 to 30 mg/kg.

The galactosamine/LPS mediated mortality was reduced.

10. Eosinophilia infiltration model

Compounds of the invention were administered orally to sensitised guinea-pigs at −20, −1 and +6 hours prior to antigen challenge. At 24 hours post antigen challenge the lungs were lavaged and inflammatory cells isolated by centrifugation. The resultant pellet was lysed and the lysate assayed for eosinophil perioxidase activity which was used as a marker for eosinophil number. Lysate eosinophil peroxidase in treated animals was compared to vehicle treated controls.

11. Bronchoconstriction model

Bronchoconstriction was induced in mechanically ventilated (guinea-pigs by administering 30 breaths of an aerosol of 0.001% w/v leukotriene D4.

Bronchoconstriction was allowed to develop to a maximum. Compounds of the invention were administered intravenously and the reduction in bronchoconstriction measured and compared to vehicle treated controls.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer amounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the amounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum amount, while in other cases the upper limit mentioned must be exceeded. In the case of administration of relatively large amounts, it is advisable to divide these into several individual doses over the course of the day.

Solvents

I petrolether:ethylacetate 1:1
II petrolether:ethylacetate 5:1
III petrolether:ethylacetate 5:2
IV ethylacetate
V dichlormethane:methanol 5:1
VI dichlormethane
VII cyclohexan:ethylacetate 3:1
VIII dichlormethan:methanol 50:1
IX dichlormethan:methanol 20:1
X cyclohexan:ethylacetate 2:1

Starting compounds

Example I

3-Amino-2-(2,4-dichlorobenzoyl)-6-methyl-7-pyridofuran

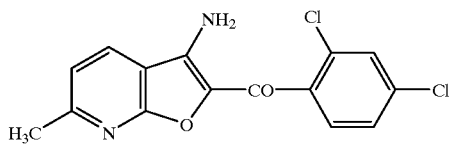

1.34 g (10 mmol) of 3-Cyano-6-methylpyridon, 4.14 g (30 mmol) K$_2$CO$_3$ and 3.21 g (12 mmol) of ω-Brom-2,4-dichloroacetophenone were suspended in 50 ml aceton. After reflux for 48 hours it was filtered off. The solvent was removed and the residue recrystallized from ethylacetate and dried.

Yield: 0,7 g (21.8%)

mp.: 237° C.

Example II

2-Hydroxy-6-methoxy-nicotinaldehyde

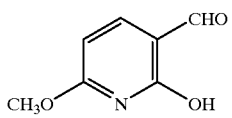

8.4 g (0.05 mol) 2,6-dimethoxy-nicotinaldehyde was solved in 75 ml methylene chloride. At 0° C. (0.2 mol) BCl$_3$ as 1 molar solution in methylene chloride 200 ml was added and stirred at room temperature for 20 h. The mixture was poured on ice/water, neutralized and extracted with CH$_2$Cl$_2$. Evaporation of the solvent affords 5.7 g (75%) of the title compound.

Example III

2-Hydroxy-6-methoxy-nicotinonitrile

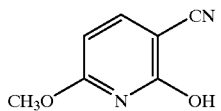

5.7 g (37 mmol) of Example III, 3.1 g (44 mmol) hydroxylamine hydrochloride and 5.1 g (74 mmol) in 50 ml formic acid were stirred under reflux for 15 h. After cooling the mixture was poured on 30 ml ice/water. Extraction with ethyl acetate, evaporation of the solvent and recrystallisation with ethanol yielded 1.2 (22%) of the title compound.

mp.: 232° C.

Example IV (3-Amino-6-methoxy-3a, 7a-dihydro-furo(2,3-b)-pyridin-2-yl)-(2,4-dichlorophenyl)-methanol

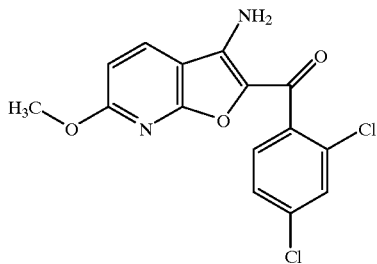

Starting from Example XIII, the title compound was prepared in analogy to example I.

Yield: 94%, mp.: 259–60° C.

Example V (3-Amino-6-hydroxy-3a,7a-dihydro-furo(2,3-b)pyridine-2-yl)-(2,4-dichlorophenyl)methanone

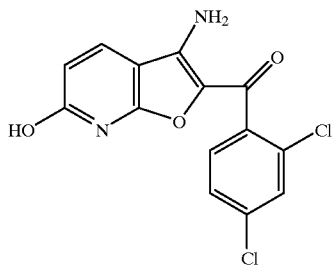

1 g (3 mmol) of Example IV was solved in 25 ml toluene. 2.8 g (21 mmol) AlCl$_3$ was added in portions at 25° C. The mixture was then stirred under reflux for 1 h. After cooling the mixture was poured on ice. Extraction with ethylacetate; evaporating the solvent and recrystallisation with ethylacetate yielded 0.73 g (75.3%) of the title compound.

mp.>305° C.

The compounds shown in table I, II, III and IV are prepared in analogy to example 1.

TABLE I

| Exp.-No. | R$^4$ | R$^5$ | Yield (%) | mp. (° C.) |
|---|---|---|---|---|
| VI | 2,5-dimethylphenyl | —CH$_3$ | 40 | 184 |

TABLE II

| Ex.-No. | R$^4$ | Yield (%) | mp. (° C.) | R$_f$ |
|---|---|---|---|---|
| VII | 3-pyridyl | 24 | — | 0,6 (V) |
| VIII | 4-pyridyl | 34 | 269 | 0,26 (V) |
| IX | 2,5-dimethylphenyl | 50 | 216–7 | — |
| X | 2,5-dimethoxyphenyl | 56 | 188 | 0,19 (Cy/EE 1/1) |

TABLE III
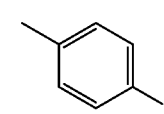
| Ex.-No. | R⁴ | Yield (%) | mp. (° C.) | $R_f$ |
|---|---|---|---|---|
| XI | 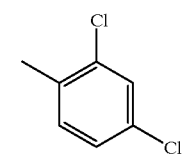 | 45 | >300 | 0,51 (I) |
| XII | 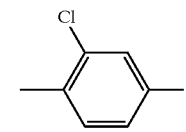 | 21 | >300 | 0,8 (V) |
TABLE III-continued
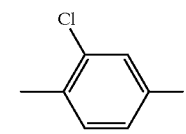
| Ex.-No. | R⁴ | Yield (%) | mp. (° C.) | $R_f$ |
|---|---|---|---|---|
| XIII | 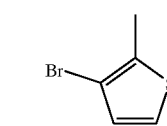 | 35 | 233 (Z) | 0,35 (I) |
TABLE IV
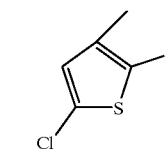
| Ex.-No. | Q | R⁴ | A | D | Yield (%) | mp. (° C.)/$R_f$ |
|---|---|---|---|---|---|---|
| XIV | S | (2,4-diCl-phenyl) | COCH₃ | H | 22 | 230–32 0.62 (cyclohexan/THF 3:7) |
| XV | S | (2,4-diCl-phenyl) | CH₃ | H | 66 | 170–71 0.48 (cyclohexan/THF 3:7) |
| XVI | O | (3-Br-2-methylthiophene) | CH₃ | H | 30 | 105 0.35 (VII) 0.86 (I) |
| XVII | O | (2,5-diCl-3-methylthiophene) | CH₃ | H | 15 | 195 0.93 (V) 0.17 (VII) 0.64 |

TABLE IV-continued

[Structure: 3-amino-furo[2,3-b]pyridine-2-carbonyl-R⁴ with substituents A (position 6), D (position 4), Q in the furan ring]

| Ex.- No. | Q | R⁴ | A | D | Yield (%) | mp. (° C.)/R$_f$ |
|---|---|---|---|---|---|---|
| XVIII | O | 2-methylthiophene | CH$_3$ | CH$_3$ | 18 | 128<br>0.93 (V)<br>0.14 (I) |
| XIX | O | 2-methylthiophene | CH$_3$ | H | 9 | amorph<br>0.12 (VII)<br>0.52 (I) |
| XX | O | 5-chloro-2-methylthiophene | CH$_3$ | H | 20 | 239<br>0.15 (VII)<br>0.57 (I)<br>0.93 (V) |
| XXI | O | 2,4-dichlorophenyl | C$_2$H$_5$ | H | 19 | 0.19 (X) |
| XXII | O | 2,4-dichlorophenyl | CH(CH$_3$)$_2$ | H | 52.6 | 0.2 (X) |
| XXIII | O | 2,4-dichlorophenyl | CH$_2$CH(CH$_3$)$_2$ | H | 39.2 | 0.19 (X) |
| XXIV | O | 2,4-dichlorophenyl | CH$_2$Br | H | 38.8 | 0.33 (X) |
| XXV | O | 2,4-dichlorophenyl | CH$_2$OCOCH$_3$ | H | 92 | 0.25 (X) |
| XXVI | O | 2,4-dichlorophenyl | CH$_2$OCH$_3$ | H | 100 | 0.13 (X) |

TABLE IV-continued

| Ex.- No. | Q | R⁴ | A | D | Yield (%) | mp. (° C.)/R$_f$ |
|---|---|---|---|---|---|---|
| XXVII | O | 2,4-dichlorophenyl | $C_3H_7$ | H | | |
| XXVIII | O | 3-chlorophenyl | $CH_3$ | H | 31 | 202–3 |
| XXIX | O | 4-fluorophenyl | $CH_3$ | H | 51 | 225 |
| XXX | O | 4-chlorophenyl | $CH_3$ | H | 56 | 255–8 |
| XXXI | O | 3,5-dichloro-2-pyridyl | $CH_3$ | H | 77 | 249–52 |

Example XXXII 4,6 Dimethoxy nicotinoaldehyde

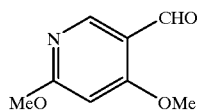

0,63 g (3,72 mmol) of 2,4-dimethyl-5-hydroxy methyl-pyridin was dissolved in 15 ml methylene chloride. After addition of 1,3 g (14.9 mmol) of $MnO_2$ the mixture was refluxed for 3 hours. After cooling the mixture was filtered off. Evaporation of the solvent affords 0,48 g (96,7%) of the title compound mp: 97–8° C.

Example XXXIII

6-Hydroxy-4-methoxy-nicotinaldehyde

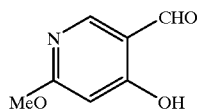

starting from example XXXII, the title compound was prepared in analogy to example II Yield: 43%, R$_f$ 0,83 (IX)

Example XXXIV

6-Hydroxy-4-methoxy-nicotinonitrile

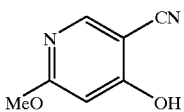

Starting from example XXXIII, the title compound was prepared in analogy to example III Yield: 26%, R$_f$=0,16 (IX)

2,4-Dimethyl-6-hydroxy-nicotinonitrile, 2,4-Dimethoxy-5-hydroxymethyl-pyridin were prepared according to the literature.

Example XXXV

4-Chloro-6-hydroxy-picolinonitile

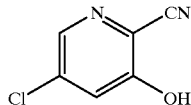

To 3-chloro-5-hydroxy-N-oxide (prepared from the corresponding pyridine using 30% $H_2O_2$ and acetic acid) (3.64 g, 25 mmol) in dry acetonitrile (20 ml) were added triethylamine (8.3 ml, 62.5 mmol) and trimethylsilyl cyanide (I ml, 87.5 mmol), dropwise at rt. The resulting mixture was heated at 100–110° C. for 8 hours. After cooling to rt, the solvent and unreacted reagents were evaporated, the residue was refluxed for 0.5 hour with hexamethyldisilazane. It was concentrated again under reduced pressure and the crude product was purified by column chromatography to afford 1.25 g (32% yield) of the desired product.

Compounds shown in Table V are prepared in analogy to example I

TABLE V

| Ex.-No | $R^4$ | A | G | E | Yield | m.p. |
|---|---|---|---|---|---|---|
| XXXVI | 2,4-dichlorophenyl | —$OCH_3$ | N | CH | 67% | 173(d) |
| XXXVII | 2,4-dimethylphenyl | —$CH_3$ | N | C—$CH_3$ | 94% | — |
| XXXVIII | 2,4-dichlorophenyl | —Cl | CH | N | 55% | — |
| XXXIX | 2,4-dichlorophenyl | —$CH_3$ | N | C—$CH_3$ | 40% | — |

PREPARATION EXAMPLES

Example 1

[2-(2,4-Dichlorobenzoyl)-6-methyl-7-pyridofuran-3-yl]urea

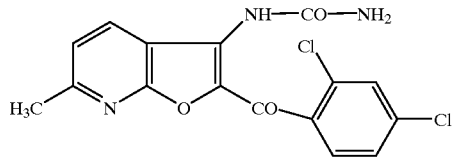

0.321 g (1 mmol) of Example 1 was solved in ethylacetate and 0.163 g/0,1 ml (1.15 mmol) chlorosulfonylisocyanat was added. After 2 hours stirring at room temperature 5 ml HCl as added and stirred until the product is formed as a precipitate. 10 ml water was added and the precipitate filtered off. The compound was washed with water and ethanol and dried.

Yield: 0.25 g (68.9%)

mp.: 217° C.

Example 2

[2-(2,4-Dichloro-benzoyl)-6-hydroxy-3a,7a-dihydrofuro[2,3b]pyridin-3-yl]-urea

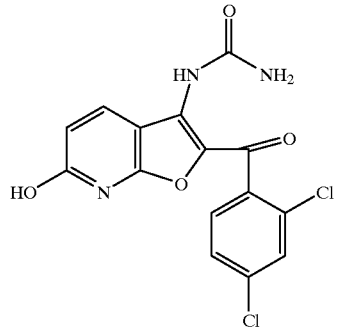

The title compound was prepared in analogy to Example 1, starting from Example V.

Yield: 86%, mp.: 200° C.

Example 3

[6-Allyloxy-2-(2,4-dichloro-benzoyl)-3a,7a-dihydrofuro[2,3-b]pyridin-3-yl]-urea

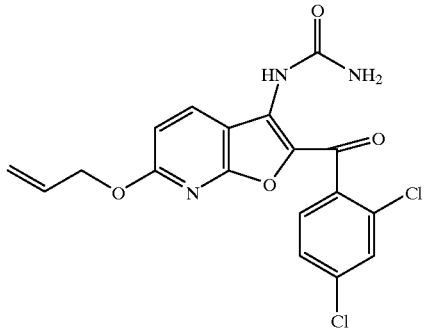

1.1 g (3 mmol) of Example 2, 0.42 g (3.45 mmol) 3-Brompropen and 0.41 g (3 mmol) $K_2CO_3$ were mixed in 30 ml acetone and refluxed for 3 h. After cooling the mixture was poured in 20 ml water. Extraction with ethyl acetate, evaporation of the solvent and recrystallisation with ethanol affords 0.12 g (9.8%) of the title compound.

mp.: 222° C.

Compounds shown in table 1, 2, 3, 4, 5 and 6 are prepared in analogy to example 1, except * marked compounds in Table 3 and 6 which are prepared in analogy to Example 3.

TABLE 1

| Ex.-No. | $R^4$ | Yield (%) | mp. (° C.) | $R_f$ |
|---|---|---|---|---|
| 4 | 3-pyridyl | 56 | 224 | — |
| 5 | 4-pyridyl | 10 | >300 | 0.09 (100/5) |
| 6 | 2,4-dimethylphenyl | 84 | 218 | — |
| 7 | 2,4-dimethoxyphenyl | 5 | — | 0.19 (VIII) |

TABLE 2

[Structure: furo-quinoline with urea-NH at 3-position and C(O)R⁴ at 2-position]

| Ex.-No. | R⁴ | Yield (%) | mp. (° C.) | R_f |
|---|---|---|---|---|
| 8 | 4-Cl-C₆H₄ | 98 | 214 | 0.08 (I) |
| 9 | 2,4-diCl-C₆H₃ | 92 | >300 | 0.05 (cyclohexan/THF 3:7) |

TABLE 2-continued

[Same structure]

| Ex.-No. | R⁴ | Yield (%) | mp. (° C.) | R_f |
|---|---|---|---|---|
| 10 | 3-Br-C₆H₄ | 90 | 237 | 0.06 (I) |

TABLE 3

[Structure: furo[2,3-b]pyridine with substituent A at 6-position, urea-NH at 3-position, C(O)R⁴ at 2-position]

| Ex.-No. | R⁴ | A | Yield (%) | mp. (° C.)/R_f |
|---|---|---|---|---|
| 11 | 2,4-diCl-C₆H₃ | —OCH₃ | 82 | 234–6 |
| 12 | 2,5-di(CH₃)-C₆H₃ | —OCH₃ | 59 | 232–4 |
| 13 | 2,6-di(CH₃)-pyridin-3-yl | —CH₃ | 10 | 224 |

TABLE 3-continued

Structure: 2-(CO-R⁴)-3-(NH-CO-NH₂)-6-A-furo[2,3-b]pyridine

| Ex.-No. | R⁴ | A | Yield (%) | mp. (° C.)/R_f |
|---|---|---|---|---|
| 14* | 2,4-dichlorophenyl | —O—CH₂—CO—N(pyrrolidine) | 94 | 255 |
| 15 | 2,4-dichlorophenyl | —C₃H₇ | 72.7 | 0.1 (X) |
| 16 | 2,5-dichloro-3-methylthiophene | CH₃ | 57 | amorph 0.10 (VII); 0.45 (I) |
| 17* | 2,4-dichlorophenyl | OCH₂CH₂N(piperidine) | 5 | 233 |
| 18* | 2,4-dichlorophenyl | OCH₂CH₂N(pyrrolidine) | 15 | 210° C. |
| 19 | 2,4-dichlorophenyl | CH₂OCH₃ | 43 | 0.24 (I) |
| 20 | 3-nitrophenyl | OCH₃ | 63 | 246° C. |
| 21 | 2,4-dichlorophenyl | C₂H₅ | 12 | 0.116 (X) |

TABLE 3-continued

[Structure: furo[2,3-b]pyridine with 3-NH-C(=O)-NH₂ (urea) group, 2-C(=O)-R⁴, and A substituent on pyridine ring]

| Ex.-No. | R⁴ | A | Yield (%) | mp. (° C.)/R_f |
|---|---|---|---|---|
| 22 | 2,4-dichlorophenyl | CH₂CH(CH₃)₂ | 67 | 0.52 (X) |
| 23 | 2,4-dichlorophenyl | CH(CH₃)₂ | 58 | 0.09 (X) |

*prepared like example 33

TABLE 4

[Structure: furo/thieno[2,3-b]pyridine with A' at 4-position, A at 6-position, 3-NH-C(=O)-NH₂, 2-C(=O)-R⁴, Q = O or S]

| Ex.-No. | A' | R⁴ | A | Q | Yield (%) | mp. (° C.) |
|---|---|---|---|---|---|---|
| 24 | H | 2,4-dichlorophenyl | COCH₃ | S | 18 | 220–22 |
| 25 | CH₃ | 2-thienyl | CH₃ | O | | |

TABLE 5

![Structure with NH-CO-NH2, H3C, N+, CH3, O, R4, Cl-]

| Ex.-No. | R⁴ | Yield (%) | mp. (° C.) |
|---------|----|-----------|-----------|
| 26* | 2,4-dichlorophenyl | 40 | 214 |

*The compound was synthesized starting from Example 1 by reaction with methyliodid in acetone under reflux

Example 27
[2-(2,4-Dichlorobenzoyl)-6-methoxy-7-pyridofuran-3-yl]urea phorphoric acid di-ethylether

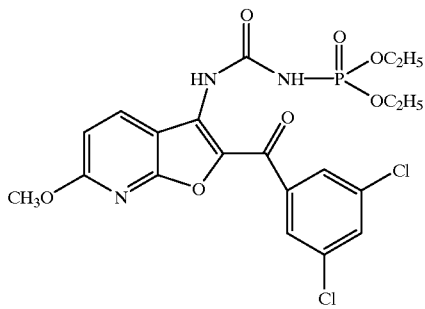

0.5 g (0.148 mmol) of Example IV was suspended in a mixture of 10 ml methylenechloride, 5 ml THF and 4 ml DMF. At 0° C. 1.3 ml (8.88 mmol). Diethoxyphosphinyl-isocyanat was added. The reaction was refluxed for 48 hours. 40 ml methylenechloride was added and the organic layer was washed twice with 5% NaHCO₃-solution, dried and isolated. The precipitate was washed with diethylether and further purified by chromatography (methylenechloride/ethanol 40/1).
Yield: 0.625 g (81.8%)
$R_f$=0.40 (methylenchloride/ethanol 40.1)

TABLE 6

| Ex.-No | A | G | M | R⁴ | Yield (% of theory) | mp.(° C.) | $R_f$ |
|--------|---|---|---|----|---------------------|-----------|------|
| 28 | —C₂H₅ | CH | N | 3-bromophenyl | 63 | — | 0.21 (X) |
| 29 | —CH₃ | N | N | 2,4-dichlorophenyl | 12 | — | — |
| 30 | —CH₃ | N | N | 2,5-dimethylphenyl | 34 | 270–2 | — |
| 31 | —CH₃ | CH | N | 3-nitrophenyl | 15 | 258 | 0.13 (VIII) |

TABLE 6-continued

[Structure: furopyridine core with urea substituent HN-C(=O)-NH₂ at position 3, C(=O)-R⁴ at position 2, with variables A, G, M]

| Ex.-No | A | G | M | R⁴ | Yield (% of theory) | mp.(° C.) | $R_f$ |
|---|---|---|---|---|---|---|---|
| 32 | —CH₃ | CH | N | 3-chlorophenyl | 41 | >280 | 0.31 (IX) |
| 33* | —OSO₂CH₃ | CH | N | 2,4-dichlorophenyl | 40 | 219–22 | — |
| 34 | —CH₃ | CH | N | 4-fluorophenyl | 60 | 238 | 0.43 (IX) |
| 35 | —CH₃ | CH | N | 4-chlorophenyl | 45 | 238 | — |
| 36 | —CH₃ | CH | N | 3,5-dichloropyridin-2-yl | 33 | 215 | — |

*The compound was synthesized starting from example 2 by reaction with methansulfonyl chloride and K₂CO₃ in DMF at 80° C. for 8 hours under reflux

TABLE 7

[Structure: furopyridine core with urea HN-C(=O)-NH-R³ at position 3, C(=O)-R⁴ at position 2, with variable A]

| Ex.-No | R⁴ | A | R³ | Procedure | Yield | m.p. |
|---|---|---|---|---|---|---|
| 37 | 2,4-dichlorophenyl | —OCH₂CH₂OCH₃ (methoxyethoxy) | H | A | 73% | |

TABLE 7-continued
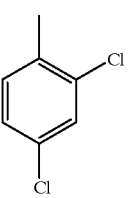
| Ex.-No | R⁴ | A | R³ | Procedure | Yield | m.p. |
|---|---|---|---|---|---|---|
| 38 | 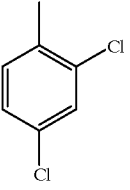 | —CH₃ | —CH₃ | B | 42% | 235° C. |
| 39 | 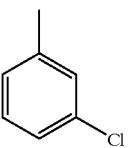 | —O—(CH₂)₄—O—C(O)CH₃ | H | A | 60% | |
| 40 | 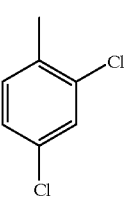 | —OCH₃ | H | B | 74% | 234° C. |
| 41 | 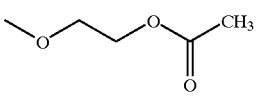 | CH₃O—CH₂CH₂—O—C(O)CH₃ | H | A | 15% | |

TABLE 8

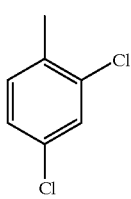

| Ex.-No | R⁴ | A | G | E | Yield | Procedure in analogy |
|---|---|---|---|---|---|---|
| 42 | 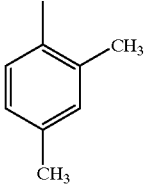 | —OCH₃ | N | CH | 18% | Ex. 1 |
| 43 | 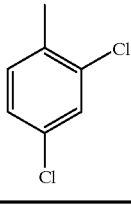 | —CH₃ | N | C—CH₃ | | Ex. 1 |
| 44 | 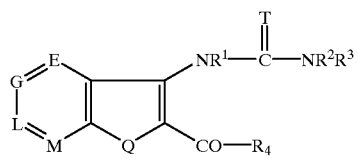 | —Cl | N | N | | Ex. 1 |

Procedure A: like example 33 with the corresponding alkylhalogenides and example 2 as starting material
Procedure B: like example 1

What is claimed is:

1. A compound of the formula (I)

$$\text{(I)}$$

in which

E, G. L and M are identical or different and represent a nitrogen atom or a residue of a formula —C—A, wherein at least one of the subltituents E, G, L or M must represent a nitrogen atom and wherein A represents hydrogen straight-chain or branched acyl or alkoxy-carbonyl each having up to 6 carbon atoms or straight-chain or branched alkyl having up to 6 carbon atoms, which is optionally substituted by carboxyl, halogen, hydroxyl, straight-chain or branched alkoxycarbonyl, or alkoxy, each having up to 6 carbon atoms, phenoxy, benzoyl or by a group of a formula —O—CO—CH₃, or represents halogen, carboxyl, cyano, nitro, trifluoromethyl, trifluoromethoxy or a group of a formula —OR⁵—, —S(O)$_a$R⁶, —(O—CH₂—CO)$_b$—NR⁷R⁸, —CO—NR⁹R¹⁰, —SO₂—NR¹¹R¹² or —NH—SO₂R¹³, in which R⁶, R⁸, R¹⁰ and R¹² are identical or different and denote hydrogen, cycloalkyl having 3 to 6 carbon atoms, benzyl or a 5 to 7-membered saturated or unsaturated heterocycle having up to 3 heteroatoms from the series comprising N, S and O and to which a phenyl ring can be fused and which is optionally substituted by identical or different substituents from the series comprising halogen, cyano, nitro or by a straight-chain or branched alkyl having up to 6 carbon atoms or denote straight-chain or branched alkenyl or acyl each having up to 8 carbon atoms, or denote phenyl, which is optionally monosubstituted to disubstituted by identical or different substituents from the series comprising nitro, halogen, carboxy or straight-chin or branched alkoxycarbonyl having up to 6 carbon atoms, R⁷, R⁹ and R¹¹ are identical or different and denote hydrogen or a straight-chain or branched alkyl having up to 4 carbon atoms, or
- R$^7$ and R$^8$ together with the nitrogen atom form a 5- to 6-membered heterocycle,
- R$^5$ has the abovementioned meaning of R$^6$, R$^8$, R$^{10}$ or R$^{12}$ and is identical or different from the latter, or
- R$^5$ denotes a hydroxyl protecting group or straight-chain or branched alkoxycarbonyl having up to 6 carbon atoms, or denotes straight-chain or branched alkyl having up to 8 carbon atoms, which is optionally substituted by carboxyl, hydroxyl, straight-chain or branched acyl or alkoxycarbonyl each having up to 6 carbon atoms, phenoxy, benzoyl or by a 5- to 7-membered unsaturated heterocycle having up to 3 heteroatoms from the series comprising N, S and/or O which is optionally substituted by halogen, cyano, nitro, or, by straight-chain or branched alkyl having up to 6 carbon atoms,
- and/or alkyl is substituted by a croup of a formula —(CO)$_g$—NR$^{14}$R$^{15}$ in which
- R$^{14}$ and R$^{15}$ are identical or different and have the above-mentioned meaning of R$^7$ and R$^8$ and
- c denotes a number 0 or 1, or
- R$^5$ denotes a group of the formula —SO$_2$—R$^{16}$
- R$^{16}$ phenyl, trifluoromethyl or straight-chain or branched alkyl having up to 4 carbon atoms,
- a denotes a number 0, 1 or 2,
- b denotes a number 0 or 1,
- R$^{13}$ has the abovementioned meaning of R$^{16}$ and is identical or different from the latter, or
- E and G represent the CH-group and
- L and M represent a residue of a formula —CD and —CD' in which
- D and D' together form a pyridine ring,
- R$^1$ represents hydrogen, straight-chain or branched alkyl having up to 6 carbon atoms, an aminoprotecting group or a group of the formula —CO—R$^{17}$ in which
- R$^{17}$ denotes hydroxyl, straight chain or branched alkoxycarbonyl having up to 6 carbon atoms, cycloalkyl having 3 to 6 carbon atoms, pyridyl, pyrrolidinyl or straight chain or branched alkyl having up to 8 carbon atoms, which is optionally substituted by halogen, carboxyl or straight chain or branched alkoxycarbonyl having up to 6 carbon atoms, or denotes phenyl, which is optionally substituted by hydroxyl, carboxyl or straight chain or branched alkoxy or alkoxycarbonyl each having up to 6 carbon atoms,
- T represents an oxygen or sulfur atom,
- R$^2$ and R$^3$ are identical or different and represent hydrogen, cycloalkyl, having up to 6 carbon atoms, straight chain or branched alkyl alkoxycarbonyl or alkenyl each having up to 8 carbon atoms, or represent benzoyl or aryl having 6 to 10 carbon atoms, which are optionally monosubstituted to trisubstituted by identical or different substituents from the series comprising halogen, cyano, nitro, carboxyl, straight-chain or branched alkyl, alkoxy, alkoxycarbonyl or acyl each having up to 6 carbon atoms, or represent a group of a formula —P(O)(OR$^{18}$(OR$^{19}$), in which
- R$^{18}$ and R$^{19}$ are identical or different and denote hydrogen or straight chain or branched alkyl having up to 6 carbon atoms, or
- R$^2$ and R$^3$ together with the nitrogen atom form a 5- to 7-membered saturated heterocycle optionally having a further O atom, and
- R$^4$ represents aryl having 6 to 10 carbon atoms or represents a 5 to 7 membered, saturated or unsaturated heterocycle, which can contain up to 4 oxygen, sulphur and/or nitrogen atoms as heteroatoms and to which further a benzene ring can be fused and wherein both rings are optionally monosubstituted to trisubstituted by identical or different substituents from the series comprising hydroxyl, halogen, nitro, 1H-tetrazolyl, pyridyl, trifluoromethyl, trifluoromethoxy, difluoromethyl, difluoromethoxy, cyano, carboxy, straight-chain or branched alkoxy, alkoxycarbonyl or acyl each having up to 8 carbon atoms or by straight-chain or branched alkyl having up to 6 carbon atoms, which is optionally substituted by carboxyl or straight-chain or branched alkoxycarbonyl having up to 5 carbon atoms or by a group of a formula —NR$^{20}$R$^{21}$, —SR$^{22}$, SO$_2$R$^{23}$ or —O—SO$_2$R$^{24}$, in which
- R$^{20}$ and R$^{21}$ have the meaning shown above for R$^7$ and R$^8$, or
- R$^{20}$ denotes hydrogen, and
- R$^{21}$ denotes straight-chain or branched acyl having up to 6 carbon atoms,
- R$^{22}$ denotes straight-chain or branched alkyl having up to 6 carbon atoms,
- R$^{23}$ and R$^{24}$ are identical or different and represent straight-chain or branched alkyl having up to 6 carbon atoms, benzyl or phenyl which are optionally substituted by trifluoromethyl, halogen or straight-chain or branched alkyl having up to 6 carbon atoms;
- Q represents an oxygen or sulfur atom.

and a salt thereof.

2. The compound according to claim 1, in which
- E, G, L and M are identical or different and represent a nitrogen atom or a residue of a formula —C—A, wherein at least one of the substituents E, G, L or M must represent a nitrogen atom and wherein
- A represents hydrogen, straight-chain or branched acyl or alkoxycarbonyl each having up to 6 carbon atoms, or straight-chain or branched alkyl having up to 5 carbon atoms, which is optionally substituted by chlorine, bromine, hydroxyl, carboxyl, straight-chain or branched alkoxycarbonyl or alkoxy each having up to 5 carbon atoms, phenoxy, benzoyl, or by a group of a formula —O—CO—CH$_3$, or represents fluorine, chlorine, bromine, nitro, trifluoromethyl or a group of a formula —OR$^5$, —S(O)$_n$R$^6$, (O—CH$_2$—CO)$_h$—NR$^7$R$^8$, —CO—NR$^9$R$^{10}$, —SO$_2$—NR$^{11}$R$^{12}$ or —NH—SO$_2$R$^{13}$, in which
- R$^6$, R$^8$, R$^{10}$ and R$^{12}$ are identical or different and denote hydrogen, cyclopropyl, cyclopentyl, cyclohexyl, chinolyl pyridyl, imidazolyl, 1,3-thiazolyl or thienyl, which are optionally substituted by identical or different substituents from the series comprising fluorine, chlorine, bromine, iodine, cyano, nitro or by a straight-chain or branched alkyl having up to 5 carbon atoms,
denote straight-chain or branched alkyl alkenyl or acyl each having up to 6 carbon atoms, or denote phenyl, which is optionally monosubstituted to disubstituted by identical or different substituents from the series comprising nitro, fluorine, chlorine bromine, iodine, carboxyl or straight-chain or branched alkoxycarbonyl having up to 5 carbon atoms, $R^7$, $R^9$ and $R^{11}$ are identical or different and denote hydrogen or a straight-chain or branched alkyl having up to 3 carbon atoms, or $R^7$ and $R^8$ together with the nitrogen atom form a pyrrolidinyl or piperidinyl ring, $R^5$ has the abovementioned meaning of $R^6$, $R^8$, $R^{10}$ or $R^{12}$ and is identical or different from the latter, or $R^5$ denotes benzyl, acetyl or tetrahydropyranyl or straight chain or branched alkoxycarbonyl having up to 4 carbon atoms, denotes straight-chain or branched alkyl having up to 6 carbon atoms, which is optionally substituted by carboxyl, hydroxyl, straight-chain or branched acyl, oxyacyl or alkoxycarbonyl each having up to 4 carbon atoms, phenoxy, benzoyl or by pyridyl, imidazolyl, thenyl or furyl, which are optionally substituted by fluorine, chlorine, bromine, cyano, nitro or by straight-chain or branched alkyl having up to 4 carbon atoms, and/or alkyl is substituted by a group of a formula —(CO)$_c$—NR$^{14}$R$^{15}$, in which $R^{14}$ and $R^{15}$ are identical or different and have the above mentioned meaning of $R^7$ and $R^8$.

and c denote, a number 0 or 1, or $R^5$ denotes a group of a formula —SO$_2$R$^{16}$, in which $R^{16}$ denotes phenyl, trifluoromethyl or straight-chain or branched alkyl having up to 3 carbon atoms, a denotes a number 0, 1 or 2, b denotes a number 0 or 1, $R^{13}$ has the abovementioned meaning of $R^{16}$ and is identical or different from the latter, or E and G represent the CH-group, and L and M represent a residue of a formulae —CD and —CD', in which D and D' together form a pyridine ring, $R^1$ represents hydrogen, straight-chain or branched alkyl having up to 4 carbon atoms, tert.butoxycarbonyl or a group of the formula —CO—R$^{17}$ in which $R^{17}$ denotes hydroxyl, straight chain or branched alkoxycarbonyl having up to 4 carbon atoms, cyclopentyl, cyclohexyl, pyridyl, pyrrolidinyl or straight chain or branched alkyl having up to 5 carbon atoms, which is optionally substituted by fluorine chlorine bromine, carboxyl or straight chain or branched alkoxycarbonyl having up to 4 carbon atoms, or denotes phenyl, which is optionally substituted by hydroxyl, carboxyl or straight chain or branched alkoxy or alkoxycarbonyl each having up to 4 carbon atoms, T represents an oxygen or sulfur atom, $R^2$ and $R^3$ are identical or different and represent hydrogen, cyclobutyl, cyclopentyl, cyclohexyl or straight-chain or branched alkyl, alkoxycarbonyl or alkenyl each having up to 6 carbon atoms, or represent benzoyl or phenyl, which are optionally monosubstituted to trisubstituted by identical or different substituents from the series comprising fluorine chlorine, bromine, iodine, carboxyl, cyano, nitro or by a straight-chain or branched alkyl alkoxy or alkoxycarbonyl each having up to 5 carbon atoms, or represent a group of a formula —P(O)(OR$^{18}$)(OR$^{19}$)

in which $R^{18}$ and $R^{19}$ are identical or different and denote straight chain or branched alkyl having up to 4 carbon atoms or $R^2$ and $R^3$ together with the nitrogen atom form a pyrrolidinyl, piperidinyl or morpholinyl ring, and $R^4$ represents phenyl or represents pyridyl, pyrimidyl, pyrryl, imidazolyl, pyrazolyl, thienyl, isothilazolyl, pyrazinyl, thiazolyl or benzo[b]thiophenyl, wherein both rings are, optionally monosubstituted to trisubstituted by identical or different substituents from the series comprising hydroxyl, fluorine, chlorine, bromine, nitro, tetrazolyl, pyridyl, trifluoromethyl, trifluoromethoxy, difluoromethyl, difluoromethoxy, cyano, carboxy, straight-chain or branched alkoxy, alkoxycarbonyl or acyl each having up to 6 carbon atoms, or by straight-chain or branched alkyl having up to 4 carbon atoms, which is optionally substituted by carboxyl or straight-chain or branched alkoxycarbonyl having up to 4 carbon atoms, and Q represents an oxygen or sulfur atom, and a salt thereof.

3. The compound according to claim 1, in which

E, G, L and M are identical or different and represent a nitrogen atom or a residue of a formula —C—A, wherein at least one of the substituents is E, G, L or M, must represent a nitrogen atom and wherein A represents hydrogen, acetyl, straight-chain or branched alkoxy or alkoxycarbonyl having up to 4 carbon atoms, straight-chain or branched alkyl having up to 5 carbon atoms, which is optionally substituted by bromine or by a group of a formula O—CO—CH$_3$, methoxy or hydroxyl or represents fluorine, chlorine, bromine, carboxyl, cyano, hydroxyl nitro, trifluoromethyl, or a group of the formula —OSO$_2$—CH$_3$, —O—CH$_2$CH=CH$_2$, —O—CH$_2$—CO-pyrrolidine, —O(CH$_2$)$_2$-pyrrolidine —O(CH$_2$)$_2$-piperidine, —O—(CH$_2$)$_4$—O—C(O)—CH$_3$ or —O—(CH$_2$)$_2$—O—(C(O)—CH$_3$ or E and G represents the CH-group, and L and M represent a residue of a formulae —CD and —CD' in which

D and D' together form a pyridine ring, $R^1$ represents hydrogen or straight-chain or branched alkyl having up to 3 carbon atoms, T represents an oxygen or sulfur atom, $R^2$ and $R^3$ are identical or different and represent hydrogen, straight-chain or branched alkyl having up to 5 carbon atoms, or represent benzoyl or phenyl, or represent a group of a formula —$P(O)(OC_2H_5)_2$, and $R^4$ represents phenyl or represents pyridyl, pyrimidyl, furyl, thienyl, imidazolyl. pyrrolyl, thiazolyl or pyrazinyl which are optionally up to difold substituted by identical or different pyridyl, nitro, fluorine, chlorine, bromine, methoxy, trifluoromethyl, cyano, or by straight-chain or branched alkyl having up to 3 carbon atoms, which is optionally substituted by carboxyl or straight-chain or branched alkoxycarbonyl having up to 3 carbon atoms and Q represents an oxygen or sulfur atom, and a salt thereof.

4. The compound according to claim 1, in which $R^1$ and $R^2$ represent hydrogen, $R^4$ represents phenyl, pyridyl or thienyl, which are optionally mono- or disubstituted by chlorine, bromine, fluorine, nitro, methoxy or straight-chain or branched alkyl having up to 3 carbon atoms.

5. Process for the preparation of 3-ureido-pyridofuranes and -pyridothiophenes according to claim 1, wherein compounds of the formula (II)

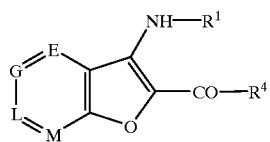 (II)

in which

E, G, L, M, $R^1$ and $R^4$ have the abovementioned meaning are reacted with compounds of the formula (III)

 (III)

in which

T has the abovementioned meaning and $R^{25}$ has the abovementioned meaning of $R_2$ and $R^3$ in inert solvents, optionally in the presence of a base and/or in the presence of an auxiliary, and in the case of $R^2/R^3$=H and T=O, compounds of the formula (II) are reacted with compounds of the formula (IIIa)

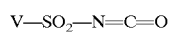 (IIIa)

in which

V denotes halogen, and in the case of $R^2/R^3$=H and T=S.

compounds of the formula (II) are reacted with $NH_4SCN$, and in case of $R^1$, $R^2$ and/or $R^3 \neq H$ the amino groups are optionally derivated and in the case of A=$OSO_2R^{16}$ the corresponding hydroxyl compounds are reacted with sulfonylchloride derivatives in presence of $K_2CO_3$.

6. A pharmaceutical composition comprising a pharmaceutically effective amount of a compound according to claim 1 and a diluent.

7. A method of treating acute and chronic inflammatory processes which comprises administering to a person in need thereof an effective amount of a compound according to claim 1.

* * * * *